US009881132B2

United States Patent
Hui (10) Patent No.: US 9,881,132 B2
(45) Date of Patent: Jan. 30, 2018

(54) METHOD AND APPARATUS FOR REMOTE WORKSTATION SYNCHRONIZATION

(71) Applicant: Change Healthcare LLC, Alpharetta, GA (US)

(72) Inventor: Jeffrey Cheuk-Lun Hui, Vancouver (CA)

(73) Assignee: CHANGE HEALTHCARE LLC, Alpharetta, GA (US)

( * ) Notice: Subject to any disclaimer, the term of this patent is extended or adjusted under 35 U.S.C. 154(b) by 746 days.

(21) Appl. No.: 13/692,384

(22) Filed: Dec. 3, 2012

(65) Prior Publication Data

US 2014/0157140 A1 Jun. 5, 2014

(51) Int. Cl.
*G06F 3/048* (2013.01)
*G06F 19/00* (2011.01)

(52) U.S. Cl.
CPC ........ *G06F 19/3418* (2013.01); *G06F 19/321* (2013.01)

(58) Field of Classification Search
CPC ..... G06F 19/322; G06F 19/327; G06F 19/321
USPC .............................................. 705/3; 715/740
See application file for complete search history.

(56) References Cited

U.S. PATENT DOCUMENTS

| 2003/0050802 | A1* | 3/2003 | Jay et al. ........................... 705/3 |
| 2005/0252971 | A1* | 11/2005 | Howarth et al. ............... 235/451 |
| 2007/0043596 | A1* | 2/2007 | Donaldson ............ G06F 19/322 705/3 |
| 2007/0170239 | A1* | 7/2007 | Hartman et al. ............... 235/375 |
| 2007/0220006 | A1* | 9/2007 | Elletson ................. G06F 19/322 |
| 2013/0132465 | A1* | 5/2013 | Brown .................... A61M 1/10 709/203 |

* cited by examiner

*Primary Examiner* — Jeffrey A Gaffin
*Assistant Examiner* — Justin Lee
(74) *Attorney, Agent, or Firm* — Alston & Bird LLP (57) ABSTRACT

Methods, apparatuses, and computer program products are described herein that are configured to provide remote access to a workstation operating in a medical domain via a zero configuration protocol. In some example embodiments, a method is provided that comprises activating a viewing application that is configured to connect to a remote workstation, via a zero configuration protocol, and enable a view of medical application data. The method of this embodiment may also include receiving an indication of a current patient context. In some example embodiments, the current patient context identifies the medical application data that is currently being viewed at the remote workstation relating a particular patient that is available for viewing in the viewing application. The method of this embodiment may also include accessing the medical application data in the viewing application based on the current patient context.

11 Claims, 4 Drawing Sheets

METHOD AND APPARATUS FOR REMOTE WORKSTATION SYNCHRONIZATION

TECHNOLOGICAL FIELD

Embodiments of the present invention relate generally to remote access technologies and, more particularly, relate to a method, apparatus, and computer program product for synchronizing a workstation and a mobile device.

BACKGROUND

Mobile devices, such as tablets, are increasing in popularity and are becoming a staple for all computer users. These mobile devices generally have processing power and computing capabilities that enable the mobile devices to be productive data consuming devices. Increasingly, traditional computer users are accomplishing more and more traditional workstation based tasks on mobile devices. Similarly, the demand to be able to accomplish workstation based tasks on a mobile device is also growing. However, in some industries and domains, the use of mobile devices to view domain specific applications is not yet standardized and, as such, viewing or interacting with the domain specific application on a mobile device is not yet available.

In some examples, access methods (e.g. browser based access methods and radio communication based methods) have been attempted for the purpose of providing access to these domain specific applications on mobile devices; however each of these access methods has resulted in, for example, limitations as to the type of data that may be viewed on the mobile device and the speed at which data can be transferred to and/or otherwise accessed by the mobile device. For example, in some wireless communication protocols, the data transfer of an image may be delayed; latent or even fail in some scenarios. Further, browser based methods may currently, for example, only provide limited views of some data that is commonly accessible via a workstation.

BRIEF SUMMARY

Methods, apparatuses, and computer program products are described herein that are configured to provide remote access to a workstation operating in a medical domain via a zero configuration protocol. In some example embodiments, a viewing application on a mobile device, such as a tablet, may subscribe to a current patient context via an adapter running in conjunction with a medical application on a workstation. The current patient context, for example, identifies medical application data that is related to a current patient that is being viewed or otherwise interacted with on a workstation, such as a picture archiving and communication system (PACS) workstation or a Radiology Information System (RIS). Using the current patient context, a user of a mobile device may then request access to the medical application data for the current patient. As such, in some example embodiments, the user of the mobile device may then access and/or otherwise store the medical application data relating to the current patient on the mobile device so as to enable viewing by the mobile device.

BRIEF DESCRIPTION OF THE DRAWINGS

Having thus described embodiments of the invention in general terms, reference will now be made to the accompanying drawings, which are not necessarily drawn to scale, and wherein:

DETAILED DESCRIPTION

Example embodiments will now be described more fully hereinafter with reference to the accompanying drawings, in which some, but not all, embodiments are shown. Indeed, the embodiments may take many different forms and should not be construed as limited to the embodiments set forth herein; rather, these embodiments are provided so that this disclosure will satisfy applicable legal requirements. Like reference numerals refer to like elements throughout. The terms "data," "content," "information," and similar terms may be used interchangeably, according to some example embodiments, to refer to data capable of being transmitted, received, operated on, and/or stored. Moreover, the term "exemplary", as may be used herein, is not provided to convey any qualitative assessment, but instead merely to convey an illustration of an example. Thus, use of any such terms should not be taken to limit the spirit and scope of embodiments of the present invention.

In some examples and in a medical domain, example connection or transmission protocols may be executed to access or otherwise synchronize application data between a mobile device (e.g. a tablet) and another computing device. For example, a radio connection via Bluetooth™ or access via a web browser. However, each of these protocols suffers from example shortcomings that arise because of the type of data in the medical domain. For example, shortcomings may include, but are not limited to, transfer speeds and/or latency when working with large medical application files (e.g. image data, audio or video files and/or the like), limitations on the type of medical application data that may be viewed (e.g. non-image data only) and/or the like.

As such, the methods, apparatuses, and computer program products as described herein, for example, are configured to enable a user of a mobile device to synchronize patient context information between a mobile device, such as a tablet, and a workstation, such as a PACS workstation. In some example embodiments, a zero configuration networking protocol may be enabled based on a zero configuration implementation library that is installed on or is accessible to a workstation and/or a mobile device. As such, in an instance in which a mobile device and the workstation are operating on a common network, such as a common wireless local area network (WLAN), the mobile device may receive an indication of a service providing remote access to medical application data on the workstation. In some example embodiments, the mobile device (e.g. based on a user setting, a user selection and/or the like) may then connect to the workstation, via the zero configuration protocol, and subscribe to or otherwise receive indications of a current patent context (e.g. a TXT record update) and any changes thereto from the service. Thus, in some example embodiments, the mobile device is enabled to view and/or store the medical application data.

Figure 1:
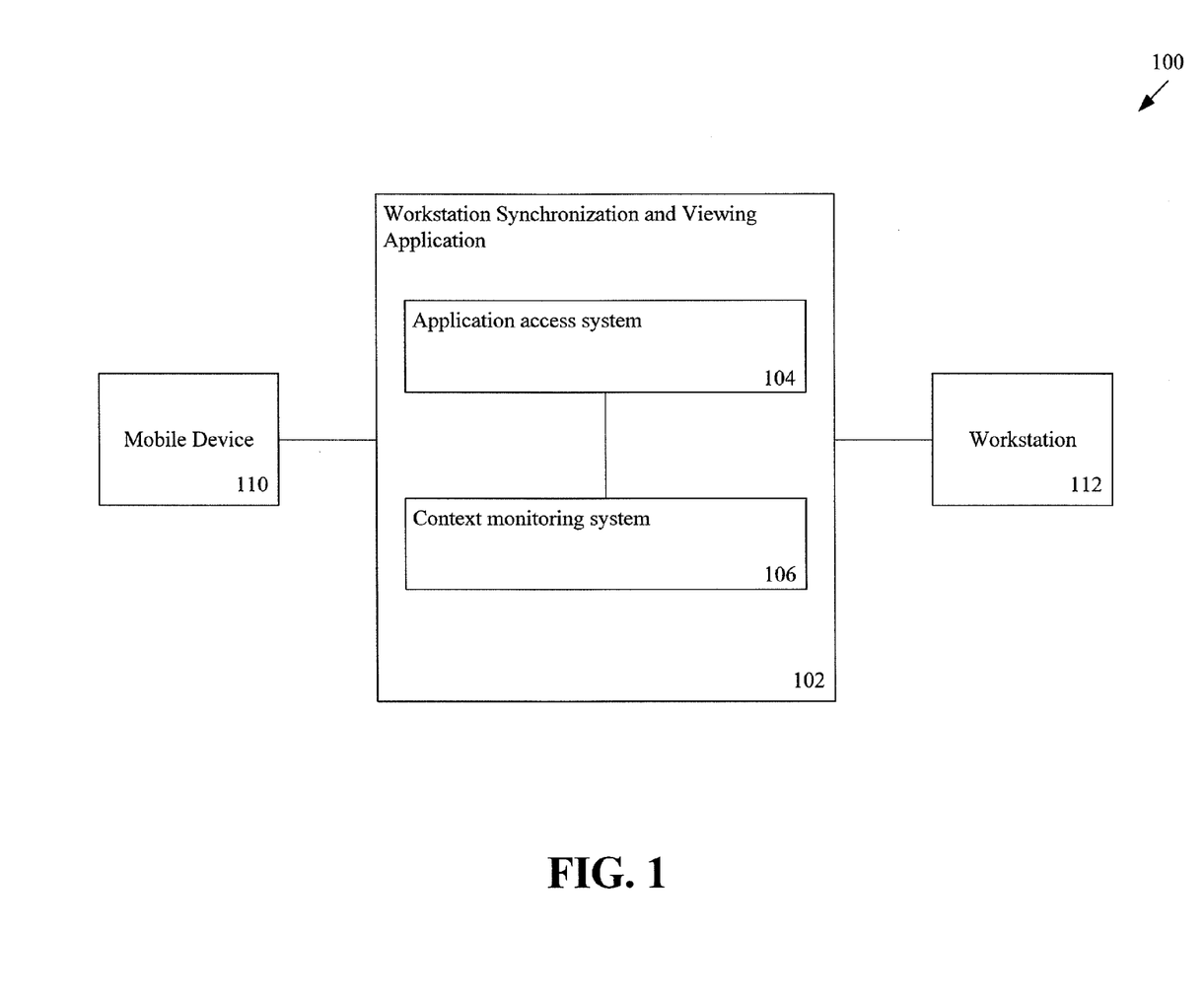
FIG. 1 is a schematic representation of a synchronization and viewing application environment that may benefit from some example embodiments of the present invention.

FIG. 1 is an example block diagram of example components of an example synchronization and viewing application environment 100. In some example embodiments, the synchronization and viewing application environment 100 comprises a workstation synchronization and viewing application 102, one or more mobile devices 110 (e.g. smart phones, tablets and/or the like) and/or one or more workstations 112 (e.g. PACS workstations, medical application workstations and/or the like). The workstation synchronization and viewing application 102 may take the form of, for example, a code module, a component, circuitry and/or the like. The components of the synchronization and viewing application environment 100 are configured to provide various logic (e.g. code, instructions, functions, routines and/or the like) and/or services related to the synchronization of and/or access to medical application data on the workstation 112. The mobile devices 110 may include, but are not limited to mobile phones, smart phones, personal digital assistants, tablets and/or the like.

In some example embodiments, the workstation synchronization and viewing application 102 may operate on and/or be embodied by the mobile device 110 and/or the workstation 112. In some example embodiments, the workstation synchronization and viewing application 102 may operate on and/or be embodied by the mobile device 110 and the workstation 112, so as to enable the mobile device 110 and the workstation 112 to synchronize medical application data and/or otherwise enable medical application data on the workstation 112 to be viewable on the mobile device 110. Alternatively or additionally, the workstation synchronization and viewing application 102 may be operating remotely and or partially remotely from the mobile device 110 and/or the workstation 112.

In some example embodiments and as is described herein, the mobile device 110 may be configured to connect to the workstation via the workstation synchronization and viewing application 102. The workstation synchronization and viewing application 102 enables such a connection via one or more radio enabled communication protocols, such as a zero configuration protocol. In some examples, mobile devices 110 and workstations 112 may be configured to operate on or in conjunction with the zero configuration protocol based on one or more installed zero configuration libraries.

In some example embodiments, the workstation synchronization and viewing application 102 may comprise an application access subsystem 104 and a context monitoring system 106. The application access subsystem 104, in some example embodiments, is configured to provide access to a medical application having medical application data operating on a workstation 112. For example a radiology application that provides image data for the diagnosis and treatment of conditions in the body. The application access subsystem 104 may connect or otherwise interact with the medical application program via an adapter, an application programming interface, a plugin and/or the like. In some example embodiments, the connection with the medical application may result in synchronization of medical application data between a mobile device 110 and a workstation 112.

For example and according to some example embodiments, the application access subsystem 104 may connect to or otherwise access the medical application via an OAF (Other Application Framework) adapter operating on a PACS workstation. In some examples, an OAF adapter (e.g. Patient Editor, Study Editor, Report Viewer and/or the like) plugs into a PACS workstation OAF framework that is configured to query or execute an adapter's functionalities, such as display a report, start dictation and/or the like. In some examples, an adapter can subscribe to events from the CSF (Context Sharing Framework) framework, which works alongside the OAF framework, to enable the detection of current patient context change events so as to enable the context monitoring system 106 to stay in sync with the medical application that is operating on the PACS workstation.

As such, and by way of example, in an instance in which a mobile device 110 and a workstation 112 are operating on the same network, such as a WLAN, the application access subsystem 104 may be configured to enable the connection between the mobile device 110 and the workstation 112 via the zero configuration protocol. For example, the workstation 112, such as via the application access subsystem 104, may register for a name (e.g. Workstation Synchronization). Then, and in an instance in which a mobile device 110 access the same network, the mobile device 110 may see or otherwise be notified via the application access subsystem 104, that a service, such as Workstation Synchronization, is accessible and thus can make the connection and thereby enable the mobile device 110 to access medical application data on the workstation 112. The connection may be made automatically or in response to a user interaction. Advantageously, for example, no additional configuration is required by the mobile device 110 or the user of the mobile device 110. Alternatively or additionally, the mobile device 110 may be required and/or otherwise configured to provide an identification to access the workstation 112 via the zero configuration protocol for purposes of security, privacy, compliance and/or the like.

In some example embodiments, the context monitoring system 106 is configured to monitor and/or otherwise subscribe to a current patient context. In some examples, the current patient context is identified by the workstation based on the current medical application data, related to a particular patient that is being worked on or is otherwise being viewed at the workstation. For example, the current patient context may identify "John" in an instance in which John's medical application data (e.g. medical chart, radiological images, lab work or the like) is being viewed. As such, whenever medical application data relating to a new patient is viewed on the workstation 112, the current patient context may be updated on the mobile device 110 via the context monitoring system 106. In some examples, the current patient context may be displayed on the mobile device 110 via the workstation synchronization and viewing application 102.

In some example embodiments, the current patient context may be provided via a TXT value. The TXT value provides an indication of the current patient context and in some example embodiments provides a uniform resource locator (URL) so as to enable the mobile device 110 to view the medical application data relating to the current patient context on the mobile device 110 via the workstation synchronization viewing application 102. In some example embodiments, the mobile device 110, the workstation synchronization and viewing application 102 and/or the like may be configured to generate a URL based on the TXT value. In some examples, a change of current patient context may be determined based on the detected change of the TXT value and/or based on a receipt of a TXT record change event indication. In some examples, the TXT value and/or TXT record change event indication may be encrypted or otherwise secured.

Alternatively or additionally, the mobile device may receive or otherwise synchronize medical application data for viewing on the mobile device 110 using the TXT value, such as via one or more network sockets. For example, the medical application data for patient "John" may be transferred to the mobile device 110 for viewing and interaction. As such, the medical application data may be viewed via the workstation synchronization and viewing application 102, by a browser and/or the like. Therefore enabling a user of a mobile device 110 to view and/or interact with image and non-image based medical application data on a mobile device.

As such, and in some examples, the medical application data may be synchronised and/or otherwise stored on the mobile device 110 to enable the viewing of the medical application data in remote location (e.g. hospital setting where radio communication is prohibited). In some examples, the mobile device 110 might belong to a patient, and the medical application data may be synchronized and/or otherwise stored on the mobile device 110 for the patient's own personal health record. Advantageously, for example, a user of a mobile device 110 may view and/or interact with medical application data without additional configuration.

Figure 2:
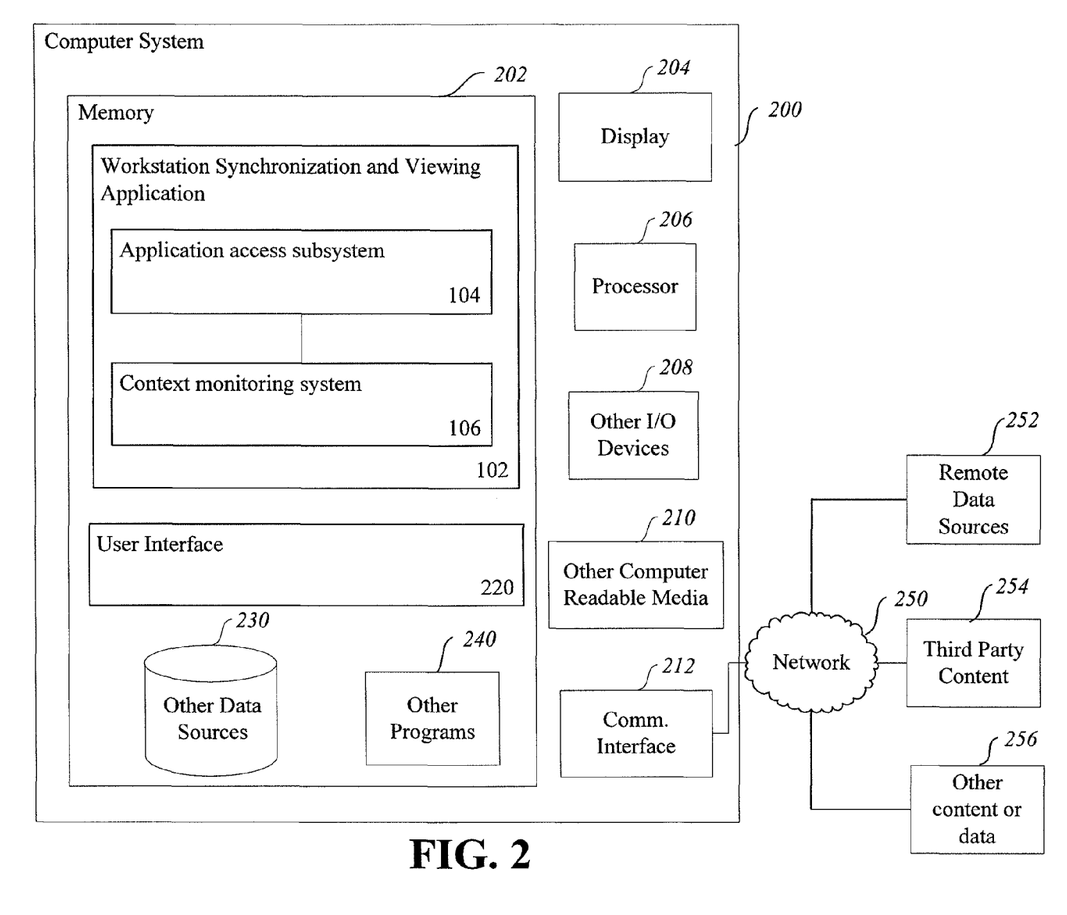
FIG. 2 illustrates a block diagram of an apparatus that embodies a workstation synchronization and viewing application that may be embodied by a mobile device and/or a workstation in accordance with some example embodiments of the present invention.

FIG. 2 is an example block diagram of an example computing device for practicing embodiments of an example workstation synchronization and viewing application. In particular, FIG. 2 shows a computing system 200 that may be utilized to implement a synchronization and viewing application environment 100 having a workstation synchronization and viewing application 102 including, in some examples, an application access subsystem 104, a context monitoring system 106 and/or a user interface 220. One or more general purpose or special purpose computing systems/devices may be used to implement the workstation synchronization and viewing application 102 and/or the user interface 220. In addition, the computing system 200 may comprise one or more distinct computing systems/devices and may span distributed locations. In some example embodiments, the workstation synchronization and viewing application 102 may be configured to operate remotely via the network 250. In other example embodiments, a pre-processing module or other module that requires heavy computational load may be configured to perform that computational load and thus may be on a remote device or server. For example, the context monitoring system 106 may be accessed remotely. In other example embodiments, a mobile device may be configured to operate or otherwise access the workstation synchronization and viewing application 102. Furthermore, each block shown may represent one or more such blocks as appropriate to a specific example embodiment. In some cases one or more of the blocks may be combined with other blocks. Also, the workstation synchronization and viewing application 102 may be implemented in software, hardware, firmware, or in some combination thereof to achieve the capabilities described herein.

In the example embodiment shown, computing system 200 comprises a computer memory ("memory") 202, a display 204, one or more processors 206, input/output devices 208 (e.g., keyboard, mouse, CRT or LCD display, touch screen, gesture sensing device and/or the like), other computer-readable media 210, and communications interface 212. The processor 206 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an application-specific integrated circuit (ASIC) or field-programmable gate array (FPGA), or some combination thereof. Accordingly, although illustrated in FIG. 2 as a single processor, in some embodiments the processor 206 comprises a plurality of processors. The plurality of processors may be in operative communication with each other and may be collectively configured to perform one or more functionalities of the workstation synchronization and viewing application as described herein.

The workstation synchronization and viewing application 102 is shown residing in memory 202. The memory 202 may comprise, for example, transitory and/or non-transitory memory, such as volatile memory, non-volatile memory, or some combination thereof. Although illustrated in FIG. 2 as a single memory, the memory 202 may comprise a plurality of memories. The plurality of memories may be embodied on a single computing device or may be distributed across a plurality of computing devices collectively configured to function as the workstation synchronization and viewing application or system. In various example embodiments, the memory 202 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof.

In other embodiments, some portion of the contents, some or all of the components of the workstation synchronization and viewing application 102 may be stored on and/or transmitted over the other computer-readable media 210. The components of the workstation synchronization and viewing application 102 preferably execute on one or more processors 206 and are configured to enable operation of a workstation synchronization and viewing application, as described herein.

Alternatively or additionally, other code or programs 240 (e.g., an administrative interface, one or more application programming interface, a Web server, and the like) and potentially other data repositories, such as other data sources 230, also reside in the memory 202, and preferably execute on one or more processors 206. Of note, one or more of the components in FIG. 2 may not be present in any specific implementation. For example, some embodiments may not provide other computer readable media 210 or a display 204.

The workstation synchronization and viewing application 102 is further configured to provide functions such as those described with reference to FIG. 1. The workstation synchronization and viewing application 102 may interact with the network 250, via the communications interface 212, with remote data sources 252 (e.g. remote medical application data and/or the like), third-party content 254 and/or other content or data 256. The network 250 may be any combination of media (e.g., twisted pair, coaxial, fiber optic, radio frequency), hardware (e.g., routers, switches, repeaters, transceivers), and protocols (e.g., TCP/IP, UDP, Ethernet, Wi-Fi, WiMAX, Bluetooth) that facilitate communication between remotely situated humans and/or devices. For example, the network may enable a zero configuration protocol, such as Bonjour, over a Wi-Fi connection. In this regard, the communications interface 212 may be capable of operating with one or more air interface standards, communication protocols, modulation types, access types, and/or the like.

In an example embodiment, components/modules of the workstation synchronization and viewing application 102 are implemented using standard programming techniques. For example, the workstation synchronization and viewing application 102 may be implemented as a "native" executable running on the processor 206, along with one or more static or dynamic libraries. In other embodiments, the workstation synchronization and viewing application 102 may be implemented as instructions processed by a virtual machine that executes as one of the other programs 240. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), and declarative (e.g., SQL, Prolog, and the like).

The embodiments described above may also use synchronous or asynchronous client-server computing techniques. Also, the various components may be implemented using more monolithic programming techniques, for example, as an executable running on a single processor computer system, or alternatively decomposed using a variety of structuring techniques, including but not limited to, multiprogramming, multithreading, client-server, or peer-to-peer, running on one or more computer systems each having one or more processors. Some embodiments may execute concurrently and asynchronously, and communicate using message passing techniques. Equivalent synchronous embodiments are also supported. Also, other functions could be implemented and/or performed by each component/module, and in different orders, and by different components/modules, yet still achieve the described functions.

In addition, programming interfaces to the data stored as part of the workstation synchronization and viewing application 102, such as by using one or more application programming interfaces can be made available by mechanisms such as through application programming interfaces (API) (e.g. C, C++, C#, Objective C and Java); libraries for accessing files, databases, or other data repositories; through scripting languages such as XML; or through Web servers, FTP servers, or other types of servers providing access to stored data. The other data sources 230 and/or stored medical application data may be implemented as one or more database systems, file systems, or any other technique for storing such information, or any combination of the above, including implementations using distributed computing techniques.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, Web Services (XML-RPC, JAX-RPC, SOAP, and the like). Other variations are possible. Also, other functionality could be provided by each component/module, or existing functionality could be distributed amongst the components/modules in different ways, yet still achieve the functions described herein.

Furthermore, in some embodiments, some or all of the components of the workstation synchronization and viewing application 102 may be implemented or provided in other manners, such as at least partially in firmware and/or hardware, including, but not limited to one or more ASICs, standard integrated circuits, controllers executing appropriate instructions, and including microcontrollers and/or embedded controllers, FPGAs, complex programmable logic devices ("CPLDs"), and the like. Some or all of the system components and/or data structures may also be stored as contents (e.g., as executable or other machine-readable software instructions or structured data) on a computer-readable medium so as to enable or configure the computer-readable medium and/or one or more associated computing systems or devices to execute or otherwise use or provide the contents to perform at least some of the described techniques. Some or all of the system components and data structures may also be stored as data signals (e.g., by being encoded as part of a carrier wave or included as part of an analog or digital propagated signal) on a variety of computer-readable transmission mediums, which are then transmitted, including across wireless-based and wired/cable-based mediums, and may take a variety of forms (e.g., as part of a single or multiplexed analog signal, or as multiple discrete digital packets or frames). Such computer program products may also take other forms in other embodiments. Accordingly, embodiments of this disclosure may be practiced with other computer system configurations.

Figure 3:
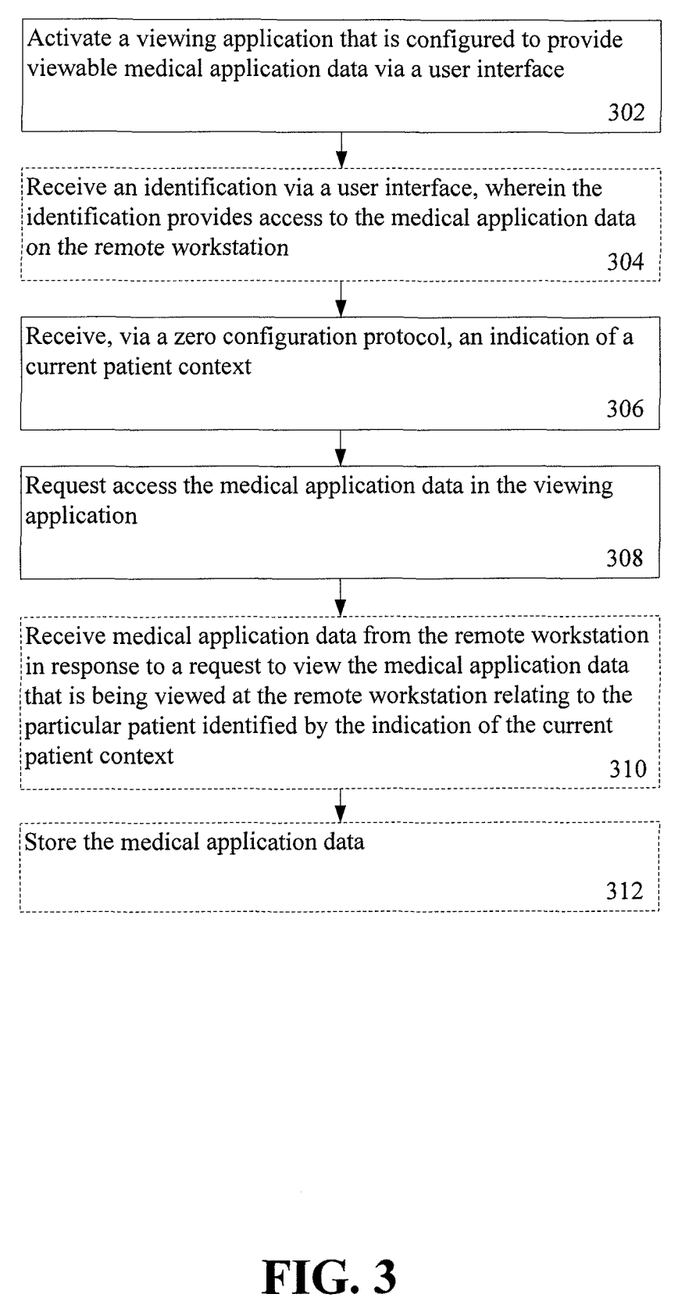
FIG. 3 illustrates a flowchart that may be performed by a mobile device in accordance with some example embodiments of the present invention.

FIG. 3 illustrates a flowchart that may be performed by a mobile device in accordance with some example embodiments of the present invention. As is shown in operation 302, an apparatus, such as the mobile device 110, may include means, such as the workstation synchronization and viewing application 102, the processor 206, or the like, for activating a viewing application that is configured to provide viewable medical application data via a user interface. In some example embodiments, the viewable medical application data is generated in a medical application on a remote workstation. For example, viewable medical application data may include medical image data that was generated by an X-ray machine that is being viewed on a workstation.

As is shown in operation 304, an apparatus, such as the mobile device 110, may include means, such as the workstation synchronization and viewing application 102, the application access subsystem 104, the processor 206, or the like, for receiving an identification via a user interface. In some example embodiments, the identification provides access to the service or medical application running on the remote workstation. For example, the identification may be a user access code, an access code for a specific workstation, an identification for a specific WLAN or the like and subsequent to the code being entered; the remote workstation may be accessible.

As is shown in operation 306, an apparatus, such as the mobile device 110, may include means, such as the workstation synchronization and viewing application 102, the context monitoring system 106, the processor 206, or the like, for receiving, via a zero configuration protocol, an indication of a current patient context. In some example embodiments the current patient context (e.g. TXT value) identifies the medical application data that is currently being viewed at the remote workstation relating to a particular patient.

As is shown in operation 308, an apparatus, such as the mobile device 110, may include means, such as the workstation synchronization and viewing application 102, the application access subsystem 104, the processor 206, or the like, for requesting access to the medical application data in the viewing application based on the current patient context. In some example embodiments, the medical application data may be accessed based on the current patient context. The current patient context may include a URL or may provide the basis for the mobile device to generate a URL. The URL, in some examples, may provide access to a view of the medical application data that is being viewed at the remote workstation relating to the particular patient identified by the indication of the current patient context.

As is shown in operation 310, an apparatus, such as mobile device 110, may include means, such as the workstation synchronization and viewing application 102, the processor 206, or the like, for receiving medical application data from the remote workstation in response to a request to view the medical application data that is being viewed at the remote workstation relating to the particular patient identified by the indication of the current patient context. In some example embodiments, the medical application data may be accessed via the URL or may otherwise be transferred to or accessed by the mobile device. For example, the mobile device may view the medical application data without transferring the data itself or, alternatively, may cause the transfer and storage of the data or some subset of the data. As is shown in operation 312, an apparatus, such as mobile device 110, may include means, such as the workstation synchronization and viewing application 102, the processor 206, or the like, for storing the medical application data.

Figure 4:
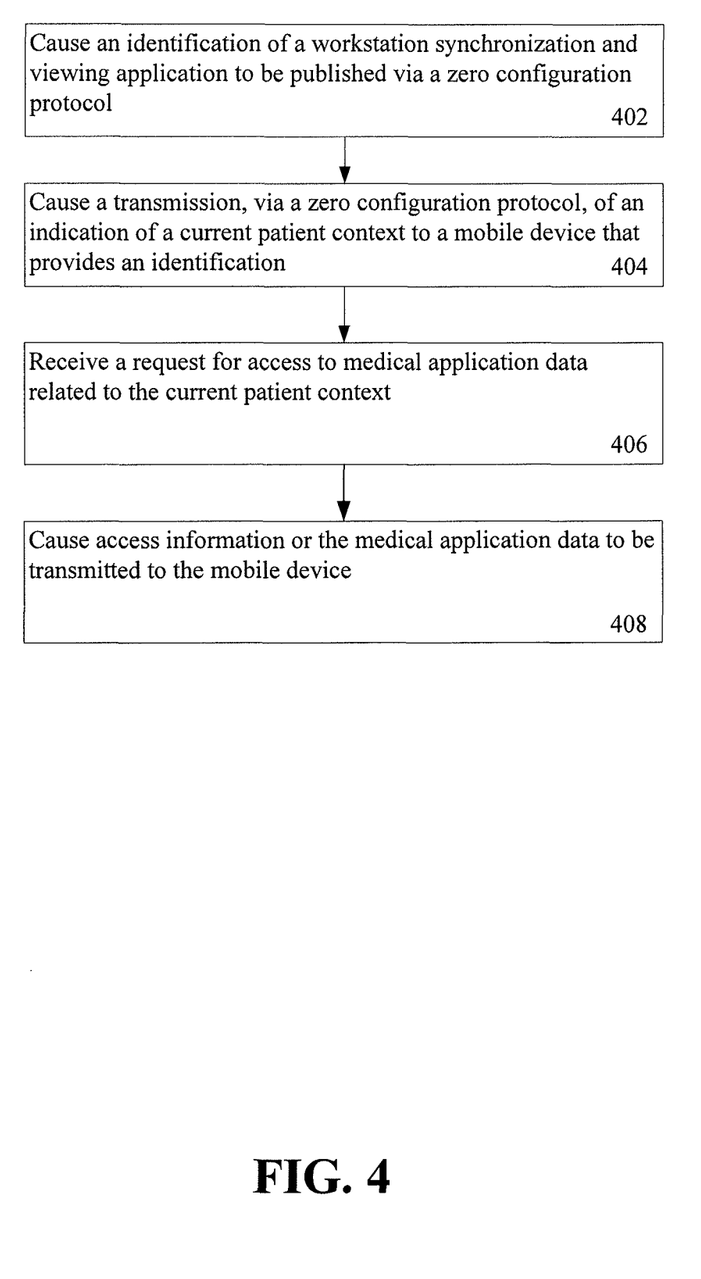
FIG. 4 illustrates a flowchart that may be performed by a workstation in accordance with some example embodiments of the present invention.

FIG. 4 illustrates a flowchart that may be performed by a workstation in accordance with some example embodiments of the present invention. As is shown in operation 402, an apparatus, such as workstation 112, may include means, such as the workstation synchronization and viewing application 102, the processor 206, or the like, for causing an identification (e.g. via the multi-cast DNS) to be published via a zero configuration protocol. In some example embodiments, the identification represents a service that the mobile device 110 can identify and connect to. As is shown in operation 404, an apparatus, such as workstation 112, may include means, such as the workstation synchronization and viewing application 102, the processor 206, or the like, for causing a transmission, via a zero configuration protocol, of an indication of a current patient context to a mobile device that provides an identification. In some example embodiments, the workstation may be configured to transmit or otherwise provide access to current patient context information (e.g. text value).

As is shown in operation 406, an apparatus, such as workstation 112, may include means, such as the workstation synchronization and viewing application 102, the processor 206, or the like, for receiving a request for access to medical application data related to the current patient context. As is shown in operation 408, an apparatus, such as workstation 112, may include means, such as the workstation synchronization and viewing application 102, the processor 206, or the like, for causing access information or, in some example embodiments, the medical application data to be transmitted to the mobile device. In some example embodiments, the access information may take the form of a URL to enable the user to view or otherwise access the medical application data. However, in other example embodiments, the access information may provide host address information to enable the transfer of the medical application data to the mobile device. In some example embodiments, the workstation may cause or otherwise allow the medical application data to be viewable on the mobile device.

FIGS. 3 and 4 illustrate example flowcharts of the operations performed by an apparatus, such as computing system 200 of FIG. 2 embodied by a mobile device or a workstation, in accordance with example embodiments of the present invention. It will be understood that each block of the flowcharts, and combinations of blocks in the flowcharts, may be implemented by various means, such as hardware, firmware, one or more processors, circuitry and/or other devices associated with execution of software including one or more computer program instructions. For example, one or more of the procedures described above may be embodied by computer program instructions. In this regard, the computer program instructions which embody the procedures described above may be stored by a memory 202 of an apparatus employing an embodiment of the present invention and executed by a processor 206 in the apparatus. As will be appreciated, any such computer program instructions may be loaded onto a computer or other programmable apparatus (e.g., hardware) to produce a machine, such that the resulting computer or other programmable apparatus provides for implementation of the functions specified in the flowcharts' block(s). These computer program instructions may also be stored in a non-transitory computer-readable storage memory that may direct a computer or other programmable apparatus to function in a particular manner, such that the instructions stored in the computer-readable storage memory produce an article of manufacture, the execution of which implements the function specified in the flowcharts' block(s). The computer program instructions may also be loaded onto a computer or other programmable apparatus to cause a series of operations to be performed on the computer or other programmable apparatus to produce a computer-implemented process such that the instructions which execute on the computer or other programmable apparatus provide operations for implementing the functions specified in the flowcharts' block(s). As such, the operations of FIGS. 3 and 4, when executed, convert a computer or processing circuitry into a particular machine configured to perform an example embodiment of the present invention. Accordingly, the operations of FIGS. 3 and 4 define an algorithm for configuring a computer or processor, to perform an example embodiment. In some cases, a general purpose computer may be provided with an instance of the processor which performs the algorithm of FIGS. 3 and 4 to transform the general purpose computer into a particular machine configured to perform an example embodiment.

Accordingly, blocks of the flowcharts support combinations of means for performing the specified functions and combinations of operations for performing the specified functions. It will also be understood that one or more blocks of the flowcharts, and combinations of blocks in the flowcharts, can be implemented by special purpose hardware-based computer systems which perform the specified functions, or combinations of special purpose hardware and computer instructions.

In some example embodiments, certain ones of the operations herein may be modified or further amplified as described herein. Moreover, in some embodiments additional optional operations may also be included (e.g. FIG. 3). It should be appreciated that each of the modifications, optional additions or amplifications described herein may be included with the operations herein either alone or in combination with any others among the features described herein.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

That which is claimed:

1. A method comprising:
    activating a viewing application on a mobile device that is configured to identify a remote workstation, via a zero configuration protocol, wherein the mobile device and the remote workstation are on a common wireless local area network;
    detecting, in a first text (TXT) value that is received via a zero configuration protocol, an indication that a current patient context is set to a first patient, wherein the current patient context (i) identifies a patient whose medical application data is currently being viewed at the remote workstation and (ii) is generated by a framework adapter operating on the remote workstation that is configured to detect a change in the indication of the current patient context;
    causing, in response to the current patient context being set to the first patient, a data connection to be formed between the viewing application and the remote workstation so as to display a first patient medical application data related to the first patient, wherein the data connection is formed based on a first uniform resource locator;
    detecting, in a second TXT value that is received via the zero configuration protocol, a change in the indication of the current patient context where the current patient context has been changed to a second patient, wherein the change is based on a change of medical application data being currently displayed on the remote workstation from the first patient medical application data to a second patient medical application data related to the second patient;
    generating a second uniform resource locator based on the indication of the current patient context; and
    causing the second uniform resource locator to be accessed so as to allow the second medical application data to be displayed in the viewing application, wherein the second medical application data replaces the first medical application data in the viewing application.

2. A method according to claim 1, further comprising:
    receiving medical application data from the remote workstation in response to a request to view the second medical application data that is being viewed at the remote workstation relating to the particular patient identified by the indication of the current patient context; and
    storing the medical application data.

3. A method according to claim 1, further comprising:
    receiving an identification of the remote workstation via a user interface, wherein selection of the identification enables the data connection.

4. A method according to claim 1, wherein the remote workstation is a picture archiving and communication system.

5. A computer program product comprising:
    at least one computer readable non-transitory memory medium having program code instructions stored thereon, the program code instructions, which when executed by an apparatus cause the apparatus at least to:
    activate a viewing application on a mobile device that is configured to identify a remote workstation, via a zero configuration protocol, wherein the mobile device and the remote workstation are on a common wireless local area network;
    detect, in a first text (TXT) value that is received via a zero configuration protocol, an indication that a current patient context is set to a first patient, wherein the current patient context (i) identifies a patient whose medical application data is currently being viewed at the remote workstation and (ii) is generated by a framework adapter operating on the remote workstation that is configured to detect a change in the indication of the current patient context;
    cause, in response to the current patient context being set to the first patient, a data connection to be formed between the viewing application and the remote workstation so as to display a first patient medical application data related to the first patient, wherein the data connection is formed based on a first uniform resource locator;
    detect, in a second TXT value that is received via the zero configuration protocol, a change in the indication of the current patient context where the current patient context has been changed to a second patient, wherein the change is based on a change of medical application data being currently displayed on the remote workstation from the first patient medical application data to a second patient medical application data related to the second patient;
    generate a second uniform resource locator based on the indication of the current patient context; and
    cause the second uniform resource locator to be accessed so as to allow the second medical application data to be displayed in the viewing application, wherein the second medical application data replaces the first medical application data in the viewing application.

6. A computer program product according to claim 5, further comprising program code instructions, which when executed by the apparatus, cause the apparatus at least to:
    receive medical application data from the remote workstation in response to a request to view the second medical application data that is being viewed at the remote workstation relating to the particular patient identified by the indication of the current patient context; and
    store the medical application data.

7. A computer program product according to claim 5, further comprising program code instructions, which when executed by the apparatus, cause the apparatus at least to:
    receive an identification of the remote workstation via a user interface, wherein selection of the identification enables the data connection .

8. A computer program product according to claim 5, wherein the remote workstation is a picture archiving and communication system.

9. An apparatus comprising:
at least one processor; and
at least one memory including computer program code, the at least one memory and the computer program code configured to, with the at least one processor, cause the apparatus to at least:
activate a viewing application on a mobile device that is configured to identify a remote workstation, via a zero configuration protocol, wherein the mobile device and the remote workstation are on a common wireless local area network;
detect, in a first text (TXT) value that is received via a zero configuration protocol, an indication that a current patient context is set to a first patient, wherein the current patient context (i) identifies a patient whose medical application data is currently being viewed at the remote workstation and (ii) is generated by a framework adapter operating on the remote workstation that is configured to detect a change in the indication of the current patient context;
cause, in response to the current patient context being set to the first patient, a data connection to be formed between the viewing application and the remote workstation so as to display a first patient medical application data related to the first patient, wherein the data connection is formed based on a first uniform resource locator;
detect, in a second TXT value that is received via the zero configuration protocol, a change in the indication of the current patient context where the current patient context has been changed to a second patient, wherein the change is based on a change of medical application data being currently displayed on the remote workstation from the first patient medical application data to a second patient medical application data related to the second patient;
generate a second uniform resource locator based on the indication of the current patient context; and
cause the second uniform resource locator to be accessed so as to allow the second medical application data to be displayed in the viewing application, wherein the second medical application data replaces the first medical application data in the viewing application.

10. An apparatus according to claim 9, wherein the at least one memory including the computer program code is further configured to, with the at least one processor, cause the apparatus to:
receive medical application data from the remote workstation in response to a request to view the second medical application data that is being viewed at the remote workstation relating to the particular patient identified by the indication of the current patient context; and
store the medical application data.

11. An apparatus according to claim 9, wherein the at least one memory including the computer program code is further configured to, with the at least one processor, cause the apparatus to:
receive an identification of the remote workstation via a user interface, wherein selection of the identification enables the data connection.

* * * * *